US009149211B2

(12) United States Patent
Mravyan et al.

(10) Patent No.: US 9,149,211 B2
(45) Date of Patent: Oct. 6, 2015

(54) MONITORING SYSTEM FOR PRESSURE SORE PREVENTION

(75) Inventors: David Mravyan, North York (CA); Milos Popovic, Mississauga (CA); Michael Mravyan, North York (CA)

(73) Assignee: SENSIMAT SYSTEMS INC., Woodbridge (CA)

( * ) Notice: Subject to any disclaimer, the term of this patent is extended or adjusted under 35 U.S.C. 154(b) by 1178 days.

(21) Appl. No.: 13/125,959

(22) PCT Filed: Oct. 23, 2009

(86) PCT No.: PCT/CA2009/001532
§ 371 (c)(1),
(2), (4) Date: Jun. 13, 2011

(87) PCT Pub. No.: WO2010/045741
PCT Pub. Date: Apr. 29, 2010

(65) Prior Publication Data
US 2011/0245732 A1     Oct. 6, 2011

Related U.S. Application Data

(60) Provisional application No. 61/108,217, filed on Oct. 24, 2008.

(51) Int. Cl.
*A61B 5/103*     (2006.01)
*A61B 5/117*     (2006.01)
(Continued)

(52) U.S. Cl.
CPC ............. *A61B 5/1116* (2013.01); *A61B 5/1126* (2013.01); *A61B 5/447* (2013.01);
(Continued)

(58) Field of Classification Search
CPC ...... A61B 5/4528; A61B 5/103; A61B 5/0053
USPC .......................................................... 600/587
See application file for complete search history.

(56) References Cited

U.S. PATENT DOCUMENTS 4,073,021 A    2/1978  Carlisle
4,086,388 A    4/1978  Brown
(Continued)

FOREIGN PATENT DOCUMENTS

WO       9201412       2/1992

OTHER PUBLICATIONS

International Search Report dated Jan. 15, 2010 for corresponding PCT Application No. PCT/CA2009/001532.

*Primary Examiner* — Sean Dougherty
*Assistant Examiner* — Daniel Cerioni
(74) *Attorney, Agent, or Firm* — Bret E. Field; Bozicevic, Field & Francis LLP

(57) ABSTRACT

Systems and methods for monitoring pressure at a contact surface, for applications such as pressure sore prevention. The system includes a number of force sensors positioned at different locations in relation to the contact surface, the force sensors providing a signal in proportion to the amount of force detected. The system includes a controller for receiving the signals from the force sensors and determining values associated with each force sensor. The controller is configured for comparing a first one or more values associated with a first subset of force sensors with a second one or more values associated with a second subset of force sensors, determining from the comparing whether a threshold between said first one or more values and said second one or more values has been exceeded, and controlling, based on the determining, an indicator to provide an indication to the user.

14 Claims, 17 Drawing Sheets

(51) Int. Cl.
   *A61B 5/11* (2006.01)
   *A61B 5/00* (2006.01)
   *A61G 5/10* (2006.01)

(52) U.S. Cl.
   CPC ............ *A61B 5/6892* (2013.01); *A61G 5/1043* (2013.01); *A61B 5/6894* (2013.01); *A61B 2562/0247* (2013.01); *A61B 2562/046* (2013.01); *A61G 2203/32* (2013.01); *A61G 2203/34* (2013.01)

(56) References Cited

U.S. PATENT DOCUMENTS

| | | |
|---|---|---|
| 4,727,878 A | 3/1988 | Levine |
| 4,951,334 A | 8/1990 | Maier |
| 5,253,656 A | 10/1993 | Rincoe et al. |
| 5,408,873 A | 4/1995 | Schmidt et al. |
| 5,449,002 A | 9/1995 | Goldman |
| 5,687,436 A | 11/1997 | Denton |
| 5,797,155 A | 8/1998 | Maier et al. |
| 5,839,140 A | 11/1998 | Wilkerson |
| 5,963,997 A | 10/1999 | Hagopian |
| 6,030,351 A | 2/2000 | Schmidt et al. |
| 6,041,658 A | 3/2000 | Casey |
| 6,287,253 B1 * | 9/2001 | Ortega et al. ............... 600/300 |
| 6,409,838 B1 | 6/2002 | Sakai |
| 6,415,467 B1 | 7/2002 | Bretvin |
| 6,417,777 B2 | 7/2002 | Fitzgerald et al. |
| 6,545,489 B1 | 4/2003 | Nitschke et al. |
| 6,560,803 B2 | 5/2003 | Zur |
| 6,669,286 B2 | 12/2003 | Iusim |
| 6,676,215 B1 | 1/2004 | Shah et al. |
| 6,739,008 B1 | 5/2004 | Kindrick |
| 6,823,549 B1 | 11/2004 | Hampton et al. |
| 6,829,799 B2 | 12/2004 | Kuhn |
| 6,853,306 B1 | 2/2005 | Nitschke et al. |
| 6,912,748 B2 | 7/2005 | VanSickle |
| 6,955,094 B1 | 10/2005 | Tarler |
| 7,146,666 B2 | 12/2006 | Christofferson et al. |
| 7,146,861 B1 | 12/2006 | Cook et al. |
| 7,156,467 B2 | 1/2007 | Kimmig |
| 2004/0054303 A1 | 3/2004 | Taylor |
| 2005/0165284 A1 * | 7/2005 | Gefen ........................ 600/300 |
| 2006/0065060 A1 * | 3/2006 | Ito et al. ................. 73/862.046 |
| 2008/0194995 A1 * | 8/2008 | Grady-Van Den Nieuwboer ............... 600/587 |
| 2009/0058661 A1 | 3/2009 | Gleckler et al. |
| 2009/0099480 A1 * | 4/2009 | Salgo et al. .................. 600/595 |
| 2009/0287120 A1 * | 11/2009 | Ferren et al. ................ 600/587 |

* cited by examiner

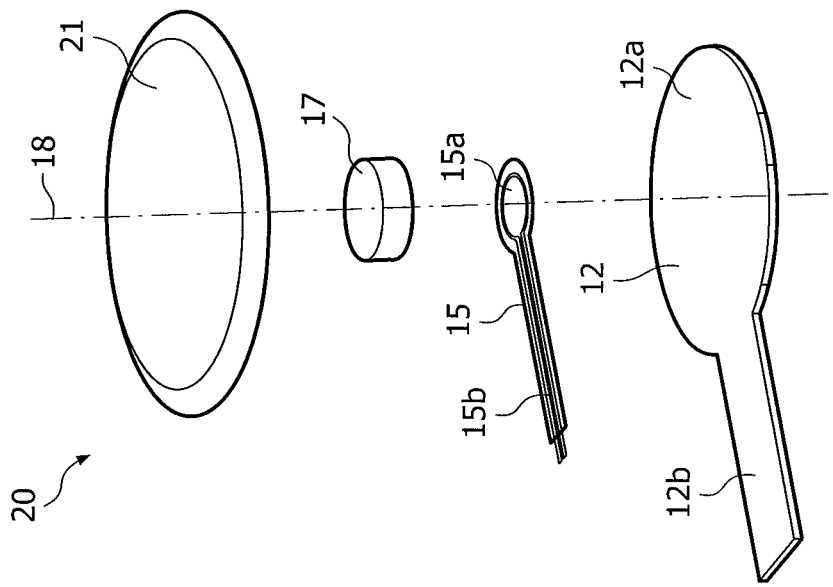
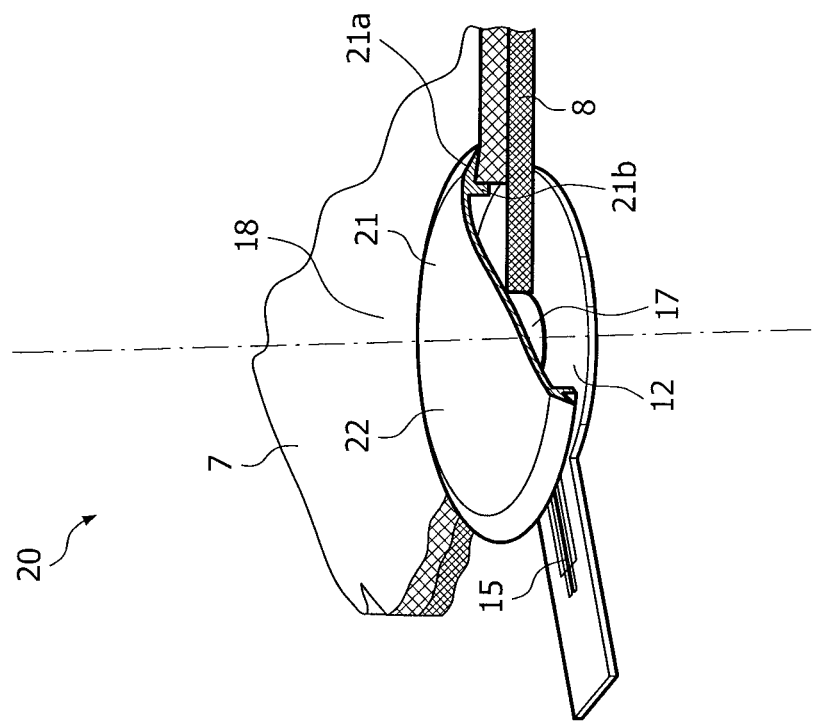

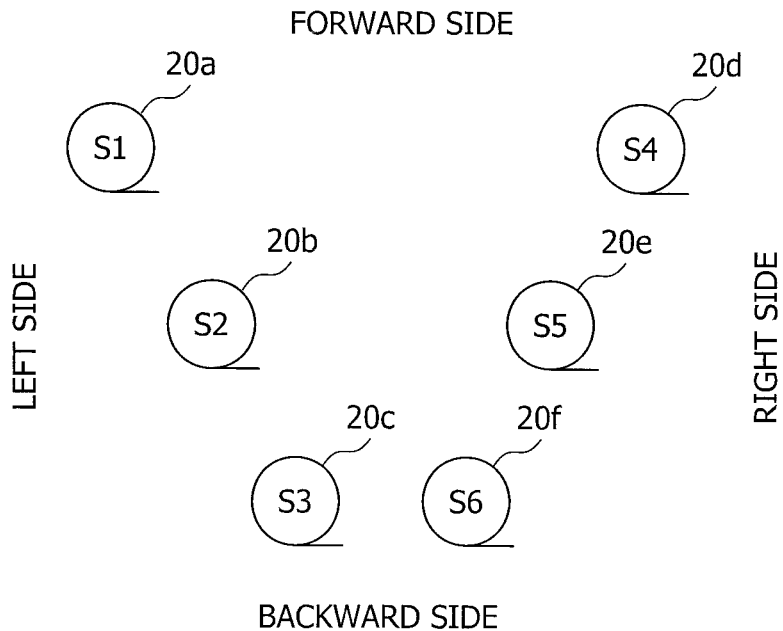

FORWARD SIDE

LEFT SIDE ... RIGHT SIDE

BACKWARD SIDE

FIG. 9A

DATA FORMATTING                                86

SUM SENSOR VALUES ALONG LEFT SIDE OF SENSING BAND (1,2,3)
=TOTAL LEFT SIDE
SUM SENSOR VALUES ALONG RIGHT SIDE OF SENSING BAND (4,5,6)
=TOTAL RIGHT SIDE
SUM TWO FRONT SENSING BAND SENSOR VALUES (1,4)
=TOTAL FORWARD
SUM TWO MIDDLE SENSING BAND SENSOR VALUES (2,5)
=TOTAL MIDDLE
SUM TWO BACK SENSING BAND SENSOR VALUES (3,6)
=TOTAL BACK
SUM FOUR FRONT SENSING BAND SENSOR VALUES (2,3,5,6)
=TOTAL BACK FOUR

FIG. 9B

PRESSURE ACQUISITION MODE TESTS

IF ((TOTAL LEFT SIDE - TOTAL RIGHT SIDE) > LEFT THRESHOLD 2) THEN ALARM, DO SIDE-TO-SIDE LEFT LEAN
IF ((TOTAL RIGHT SIDE - TOTAL LEFT SIDE) > RIGHT THRESHOLD 2) THEN ALARM, DO SIDE-TO-SIDE RIGHT LEAN
IF ((TOTAL BACK - TOTAL FORWARD) < BACK THRESHOLD 2) THEN ALARM, DO LEAN BACKWARD
IF ((TOTAL BACK - TOTAL FORWARD) > FORWARD THRESHOLD 2) THEN ALARM, DO LEAN FORWARD

FIG. 9C

POSTURE CORRECTION MODE TESTS

IF ((TOTAL LEFT SIDE - TOTAL RIGHT SIDE) > LEFT THRESHOLD) THEN ALARM, LEANING TOO FAR LEFT
IF ((TOTAL RIGHT SIDE - TOTAL LEFT SIDE) > RIGHT THRESHOLD) THEN ALARM, LEANING TOO FAR RIGHT
IF ((TOTAL FORWARD > FORWARD THRESHOLD) ||(TOTAL MIDDLE - TOTAL BACK > BACK THRESHOLD))
THEN ALARM, LEANING TOO FAR FORWARD
IF ((TOTAL BACK > TOTAL MID) && (TOTAL BACK FOUR > ALL BACK THRESHOLD)) THEN ALARM, LEANING TOO FAR BACKWARD

FIG. 9D

PRESSURE ACQUISITION MODE COMPLIANCE TESTS

SIDE-TO-SIDE LEFT LEAN:
WAIT UNTIL TOTAL LEFT SIDE - TOTAL RIGHT SIDE > LEFT THRESHOLD 3 FOR > Q TIME
(FLASH LEFT INDICATOR)
THEN WAIT UNTIL TOTAL RIGHT SIDE - TOTAL LEFT SIDE > RIGHT THRESHOLD 3 FOR > Q TIME
(FLASH RIGHT INDICATOR)
THEN WAIT UNTIL TOTAL LEFT SIDE - TOTAL RIGHT SIDE > LEFT THRESHOLD 3 FOR > Q TIME
(FLASH LEFT INDICATOR)

SIDE-TO-SIDE RIGHT LEAN:
WAIT UNTIL TOTAL RIGHT SIDE - TOTAL LEFT SIDE > RIGHT THRESHOLD 3 FOR > W TIME
(FLASH RIGHT INDICATOR)
THEN WAIT UNTIL TOTAL LEFT SIDE - TOTAL RIGHT SIDE > LEFT THRESHOLD 3 FOR > W TIME
(FLASH LEFT INDICATOR)
THEN WAIT UNTIL TOTAL RIGHT SIDE - TOTAL LEFT SIDE > RIGHT THRESHOLD 3 FOR > W TIME
(FLASH RIGHT INDICATOR)

LEAN BACKWARDS:
WAIT UNITL TOTAL BACK - TOTAL MIDDLE > MIDDLE THRESHOLD FOR > E TIME (FLASH
BACKWARD INDICATOR)

LEAN FORWARDS:
WAIT UNITL TOTAL BACK - TOTAL FORWARD < BACK THRESHOLD 3 FOR > R TIME (FLASH
FORWARD INDICATOR)

FIG. 9E

MONITORING SYSTEM FOR PRESSURE SORE PREVENTION

CROSS-REFERENCE TO RELATED APPLICATION

This application claims the benefit of the filing date of U.S. Provisional Patent Application No. 61/108,217 filed Oct. 24, 2008 under the title POSTURE CORRECTION AND PRESSURE SORE PREVENTION SYSTEM.

The content of the above patent application is hereby expressly incorporated by reference into the detailed description hereof.

FIELD

Example embodiments described herein relate generally to systems and methods for monitoring pressure at a contact surface; and, in particular, to such systems and methods for applications such as pressure sore prevention.

BACKGROUND

The skin of people confined to a bed or wheelchair is susceptible to decubitus ulcers, commonly referred to as pressure sores or bedsores.

Some existing conventional systems use a pressure relieving wheelchair cushion to prevent pressure sores together with a device which monitors pressure over time. In such systems, based on pressure readings detected and stored as a whole, an alarm is activated when an amount of pressure and time from a user has been detected; i.e., the user has been sitting for too long and is alerted to unload. A difficulty with such systems is that the user response is limited to basic unloading actions such as getting up or performing wheelchair push-ups.

Another difficulty with such systems occurs when a user is improperly sitting. If the patient develops a habit to sit with an incorrect posture, even if they comply with the unloading alerts, they are still at risk of developing pressure sores as a result of their postural deformity.

SUMMARY

In an example embodiment, there is provided a method of monitoring pressure at a contact surface for prevention of pressure sores, the contact surface for engaging a user. The method includes receiving signals from a plurality of force sensors positioned at different locations in relation to the contact surface, the force sensors providing said signals in proportion to the amount of force detected; determining values associated with each force sensor; comparing a first one or more values associated with a first subset of force sensors of the plurality of force sensors with a second one or more values associated with a second subset of force sensors of the plurality of force sensors; determining from said comparing whether a threshold between said first one or more values and said second one or more values has been exceeded; and controlling, based on said determining, an indicator to provide an indication to the user.

In another example embodiment, there is provided a pressure monitoring system for monitoring pressure at a contact surface for prevention of pressure sores, the contact surface for engaging a user. The pressure detection system includes a plurality of force sensors positioned at different locations in relation to the contact surface, the force sensors providing a signal in proportion to the amount of force detected; a controller for receiving the signals from the plurality of force sensors and determining values associated with each force sensor; and an indicator in communication with the controller. The controller is configured for comparing a first one or more values associated with a first subset of force sensors of the plurality of force sensors with a second one or more values associated with a second subset of force sensors of the plurality of force sensors, determining from said comparing whether a threshold between said first one or more values and said second one or more values has been exceeded, and controlling, based on said determining, the indicator to provide an indication to the user.

In another example embodiment, there is provided a method of monitoring pressure at a contact surface for prevention of pressure sores, the contact surface for engaging a user. The method includes receiving signals from a plurality of force sensors positioned at different locations in relation to the contact surface, the force sensors providing said signals in proportion to the amount of force detected; determining values associated with each force sensor; comparing a first one or more values associated with a first subset of force sensors of the plurality of force sensors with a second one or more values associated with a second subset of force sensors of the plurality of force sensors; determining from said comparing whether a responsive action is to be taken by the user; and controlling an indicator to provide an indication of the responsive action to be taken by the user.

BRIEF DESCRIPTION OF THE FIGURES

Embodiments will now be described by way of example with reference to the accompanying drawings, in which like reference numerals are used to indicate similar features, and in which:

FIG. 2A shows a perspective partial view of the pressure monitoring system of FIG. 1 including a force sensor in accordance with an example embodiment to be used therein;

FIG. 2B shows an exploded perspective view of the force sensor shown in FIG. 2A;

FIG. 9A illustrates in diagrammatic form a simplified distribution of the force sensors shown in FIG. 4;

FIG. 9B illustrates in detail an example data formatting module to be used in the process of FIG. 8;

FIG. 9C illustrates in detail a posture correction mode module to be used in the process of FIG. 8;

FIG. 9D illustrates in detail a pressure acquisition mode module to be used in the process of FIG. 8;

FIG. 9E illustrates in detail a pressure acquisition mode compliance test module to be used in the process of FIG. 8;

DETAILED DESCRIPTION OF EXAMPLE EMBODIMENTS

Figure 1:
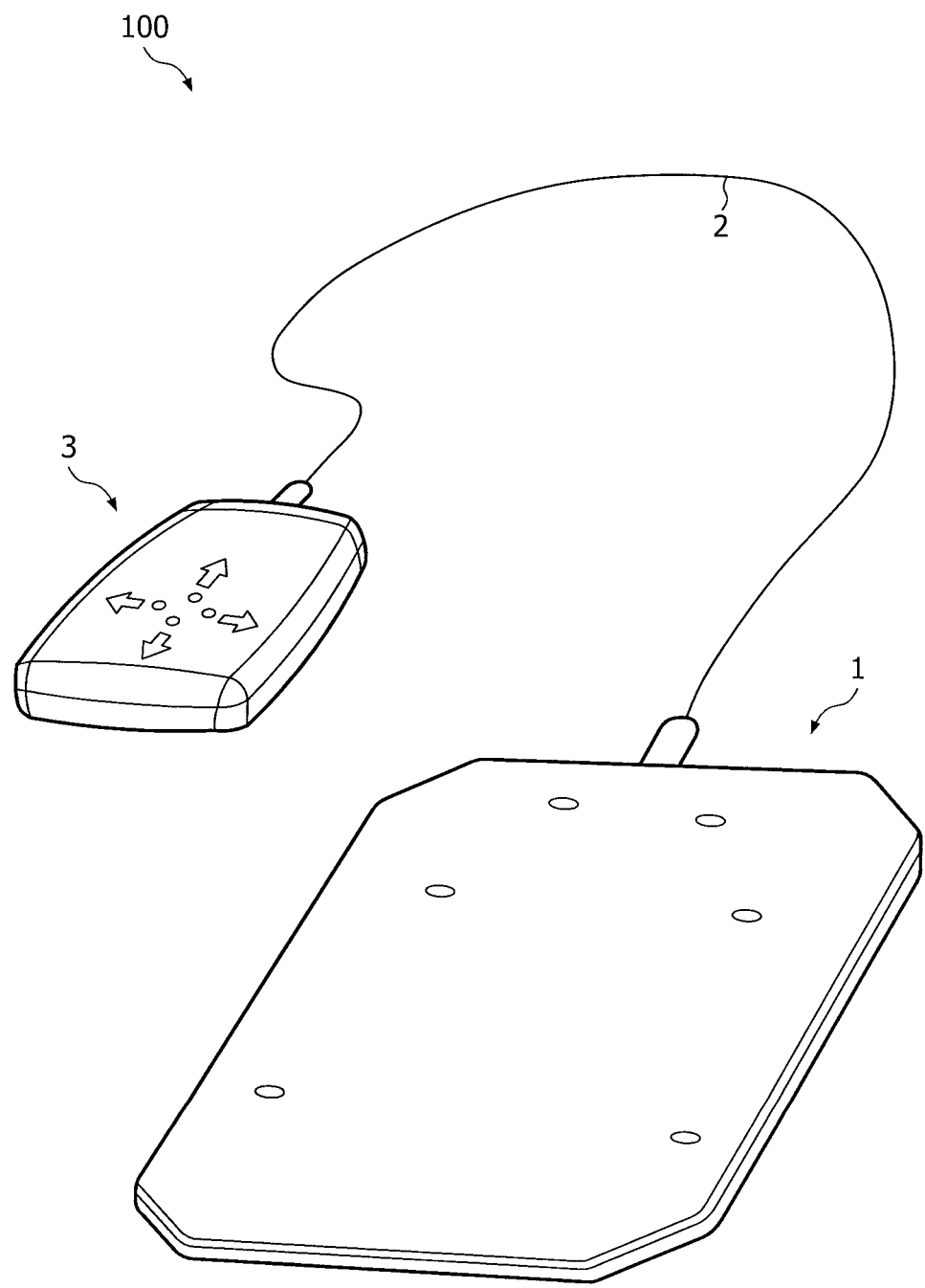
FIG. 1 shows a perspective view of a pressure monitoring system in accordance with an example embodiment.

Example embodiments relate to systems and methods for monitoring pressure at a contact surface, for applications such as pressure sore prevention.

In some example embodiments, there is generally provided a method for monitoring pressure, which includes comparing of values from a first set of force sensors with values from a second set of force sensors, determining whether a threshold between the first values and the second values has been exceeded, and providing an indication in response.

Some example embodiments relate to a non-intrusive system integrated into the wheelchair or the wheelchair cushion, and will continuously monitor the user's sitting posture and pressure distribution. This may for example be used by those user's with spinal cord injury (SCI). In the event that the system detects that the user is in a postural risk position they are notified where the area of excess pressure exists. In the event that the user is in a pressure distributive risk the system would advise him/her which new posture to assume through different exercises to mitigate the problem. By preventing pressure ulcers from occurring, individuals with SCI may reduce their sick leaves and hospitalization times, and may consequently improve their overall quality of life.

In an example embodiment, there is provided a method of monitoring pressure at a contact surface for prevention of pressure sores, the contact surface for engaging a user. The method includes receiving signals from a plurality of force sensors positioned at different locations in relation to the contact surface, the force sensors providing said signals in proportion to the amount of force detected; determining values associated with each force sensor; comparing a first one or more values associated with a first subset of force sensors of the plurality of force sensors with a second one or more values associated with a second subset of force sensors of the plurality of force sensors; determining from said comparing whether a threshold between said first one or more values and said second one or more values has been exceeded; and controlling, based on said determining, an indicator to provide an indication to the user.

In another example embodiment, there is provided a pressure monitoring system for monitoring pressure at a contact surface for prevention of pressure sores, the contact surface for engaging a user. The pressure detection system includes a plurality of force sensors positioned at different locations in relation to the contact surface, the force sensors providing a signal in proportion to the amount of force detected; a controller for receiving the signals from the plurality of force sensors and determining values associated with each force sensor; and an indicator in communication with the controller. The controller is configured for comparing a first one or more values associated with a first subset of force sensors of the plurality of force sensors with a second one or more values associated with a second subset of force sensors of the plurality of force sensors, determining from said comparing whether a threshold between said first one or more values and said second one or more values has been exceeded, and controlling, based on said determining, the indicator to provide an indication to the user.

In another example embodiment, there is provided a method of monitoring pressure at a contact surface for prevention of pressure sores, the contact surface for engaging a user. The method includes receiving signals from a plurality of force sensors positioned at different locations in relation to the contact surface, the force sensors providing said signals in proportion to the amount of force detected; determining values associated with each force sensor; comparing a first one or more values associated with a first subset of force sensors of the plurality of force sensors with a second one or more values associated with a second subset of force sensors of the plurality of force sensors; determining from said comparing whether a responsive action is to be taken by the user; and controlling an indicator to provide an indication of the responsive action to be taken by the user.

Reference is first made to FIG. 1, which shows a pressure monitoring system 100 in accordance with an example embodiment, which may for example be used for posture correction and pressure sore prevention. The pressure monitoring system 100 includes a cushion system 1 which generally includes force sensors which are connected by a multi-conducting cable 2 to a control module 3.

Figure 3:
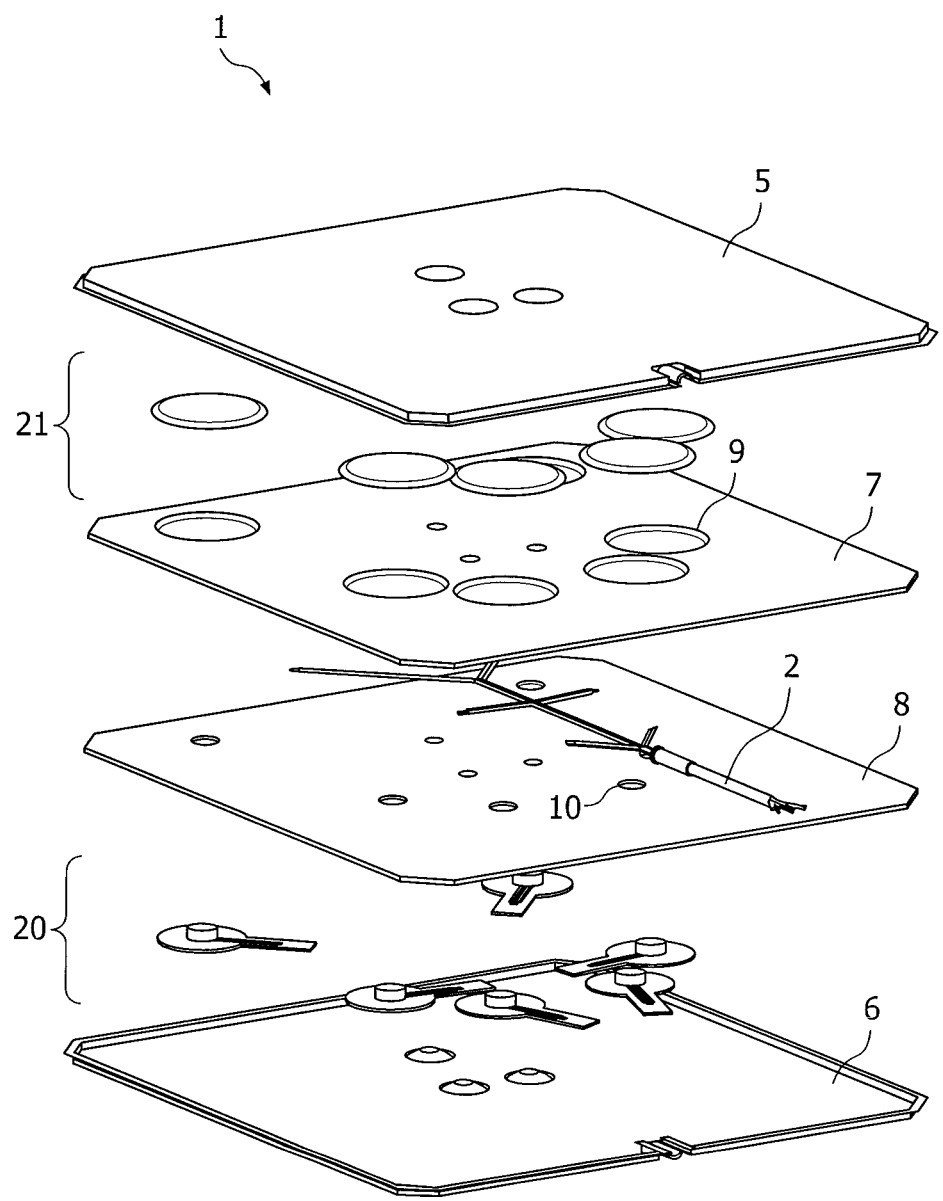
FIG. 3 shows an exploded perspective view of a cushion system including plurality of force sensors including the force sensor of FIGS. 2A and 2B to be used in the pressure monitoring system of FIG. 1.

Reference is now made to FIG. 3, which shows an exploded perspective view of the cushion system 1. The cushion system 1 includes two layers of medical fabric 5, 6, which may for example be formed from Sure Check (R) Fusion III, which for example provides a generally higher level of elasticity for environments with additional pressure management requirements. The cushion system 1 further generally provides a controlled level of stretch and recovery, which helps to prevent the mat surface from become ineffective in the pressure management due to over-elasticity. In addition, outside layers of fabric may be treated with antimicrobial additive, designed to slowly release over the life of the product. A controlled release feature allows the migration of the antimicrobial agent to the fabric surface. The antimicrobial agent helps protect the fabric from microbial attack and reduces undesirable organic odors. Outside layers of fabric are fluid and moisture resistant, reducing the risk of contamination of the cushion from liquids and bodily fluids. It is understood by those skilled in the art that moisture increases the risk of ulcer development by causing skin to weaken and break down more rapidly. Accordingly, the mentioned fabric may be used in order to minimize the development of pressure ulcers due to moisture.

Figure 5:
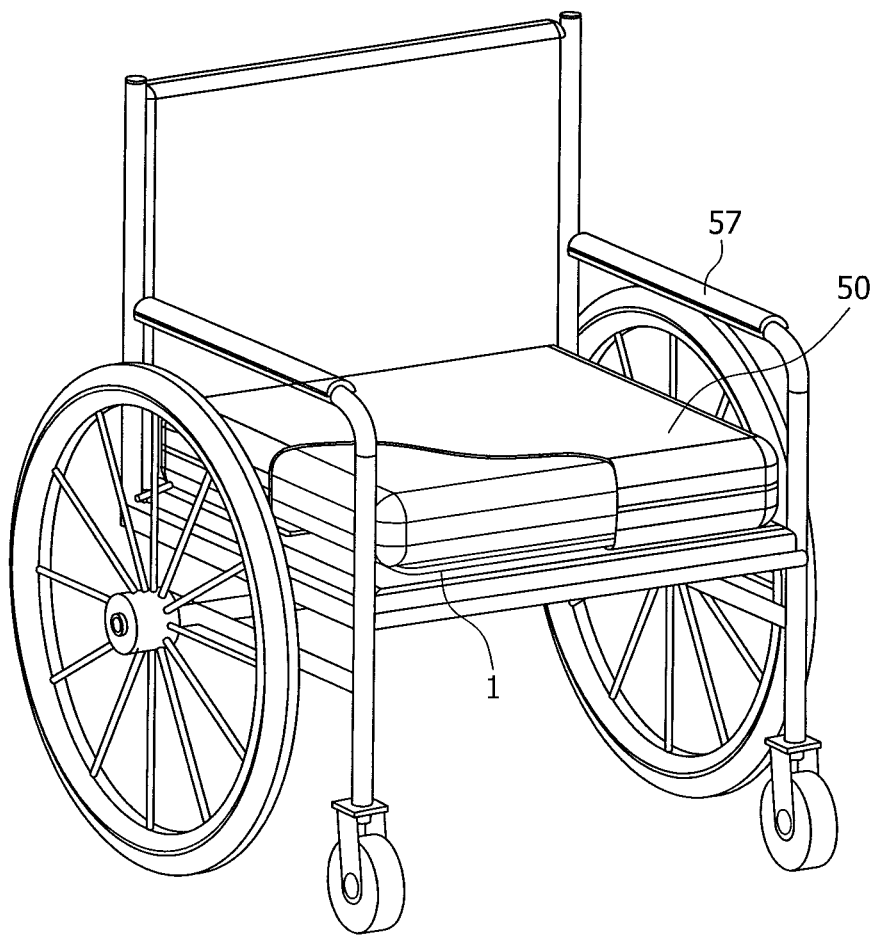
FIG. 5 shows a perspective view of a wheelchair including the pressure monitoring system of FIG. 1 in accordance with an example embodiment.

Reference is now made to FIG. 5, which shows a wheelchair 57 including use of the cushion system 1 in accordance with an example embodiment. Generally, the cushion system 1 provides uniform resistance to the weight of the patient's body and is able to accurately register the applied pressure even when inserted under an existing or conventional wheelchair cushion 50 and placed on the wheelchair 57. In other example embodiments, the cushion system 1 may for example be used within or on top of the wheelchair cushion 50. In yet further example embodiments, the cushion system 1 may include suitable padding to be used as a substitute for the wheelchair cushion 50.

Referring again to FIG. 3, in some example embodiments force sensors 20 are positioned within the cushion system 1 so that an able body person may generally not feel their presence. The two layers of medical fabric 5, 6 may be connected to each other in such a way that the top surface of medical fabric 5 is exposed outward of the cushion system 1. Between the layers of medical fabric 5, 6 are two layers of ¼" thick foam 7, 8, which are also attached to each other and attached to the both layers of medical fabric 5, 6 of the fabric along the perimeter of the cushion system 1 as well as at the certain points (three shown in FIG. 3) in the middle of the cushion system 1. The both layers of the medical fabric 5, 6 and the both layers of the foam 7, 8 are joined with each other, for example by means of the ultrasonic welding to prevent leaks from entering the cushion system 1. In an example embodiment, the cushion system 1 is designed in square or rectangular shape having all four corners chamfered at a chamfer of approximately 1", as shown.

The bottom layer of foam 8 may also be attached to the force sensors 20 which are each mounted to one of a number of rigid pads 12, as many as number of sensors 20 in the pressure monitoring system 100, for example six, as shown. Reference is now made to FIGS. 2A and 2B, which shows the force sensors in detail. Each rigid pad 12 includes a round head 12a and radial strip support 12b. Each rigid pad 12 is joined to the lower layer of the foam 8 by means of glue or other bonding technology. Each rigid pad 12 carries at least one Force Sensing Resistor (FSR) 15, which includes three layers: Flexible Substrate with printed semiconductor, Adhesive Spacer and Flexible Substrate with Printed Interdigitating Electrodes. Each resistor 15 has round active area 15a and the tail 15b with connecting leads. The force sensing resistor 15 is mounted on the rigid pad 12 in such a way that the center of the round active area 15a is located in a center, which is defined by center axis 18 of the round part 12a of the rigid pad 12 and the tail 15b of the sensor 15 is aligned along the strip 12b of the rigid pad 12. The strip 12b of the rigid pad 12 is longer than the tail 15b of the FSR 15 in order to support the incoming connector from the leads of the multi-conducting cable 2. On top of the round active area 15a of FSR 15 there is a sensor actuator 22. Sensor actuator 22 includes flexible element 17 and rigid cap 21. Flexible element 17 has a cylindrical shape with diameter equal the diameter of the active part 15a of the FSR 15 and height, which is equal to the thickness of both layers of foam 7 and 8. The bottom surface of the flexible element 17 is attached to the FSR 15 by means of glue or other technology and the top surface of the flexible element 17 is attached to the rigid cap 21 by means of glue or other technology. In other example embodiments, the sensor actuator 22 may be molded together as a single unit with the importance in dimension and durometer relationships between the flexible element 17 and the rigid cap 21. Referring now to FIGS. 2A, 2B and 3 together, the lower layer of the foam 8 has multiple, for example six, round cutouts 10, diameter of which is equal to the diameter of the flexible element 17 and centers of which are located in the same coordinates as a center of the round cutouts 9 of a larger size in the top layer of the foam 7. The top layer of the foam 7 incorporates rigid round caps 21. Each cap 21 contains an inner lip, which is perpendicular to the bottom surface of the cap 21 and has smaller diameter (diameter $D_M$) than the cap 21. The outer ridge 21a of the cap 21 is chamfered at 30 degree form the side opposite to the position of the lip, which defines the effective round area of the top surface of the cup 21. Effective area should be defined by diameter $D_M$, which is identical to the Outer Diameter (O.D.) of the inner lip 21b. At the same time the O.D of the inner lip 21b has the same diameter as the round cut out 9 of the top foam 7, so when installed the caps 21 are inserted into the top layer of the foam 7 and the outer ridges are overlaying the top layer of foam 7. The inner (bottom) side of the cap 21 is attached to the top surface of the flexible element 17 by means of glue or other bonding technology. The centers of all parts: round head of rigid pad 12a, round active area of the FSR 15a, flexible element 17, rigid round cap 21 and both round cut-outs 9 and 10 of the both layers of the foam 7 and 8 are coincident along the same axis 18 as shown in FIG. 2.

In some example embodiments, it is recognized herein that a correlation may be used between the following components of the system 100, which may be applied to various cushion sizes as appropriate, for example having specified widths as outlined below, and which are shown in Equations 1 and 2:

Equation 1
$$\frac{D_M}{d} = \frac{DU_1}{DU_2} = K, K = 3 - 3.5 \quad (1)$$

Equation 2
$$\frac{W_C}{D_M} = 2K, K = 3 - 3.5 \quad (2)$$

In Equation 1, $D_M$ is the diameter of the effective area of the cap 21, which is diameter of the inner lip 21b of the cap 21 and cutout 9 in the top layer of foam 7; d is the diameter of the round actuator 17 and cutout 10 in the bottom layer of the foam 8; $DU_1$ is the Durometer of the flexible element of the sensor actuator 17; and $DU_2$ is the Durometer of the foam layer 7,8. In Equation 2, $W_c$ is the specified width of the existing wheelchair cushion for which a specific sensor placement is intended. Some usual sizes of $W_c$ are 14"-22", with typical sizes changing in increments of 2".

Figure 4:
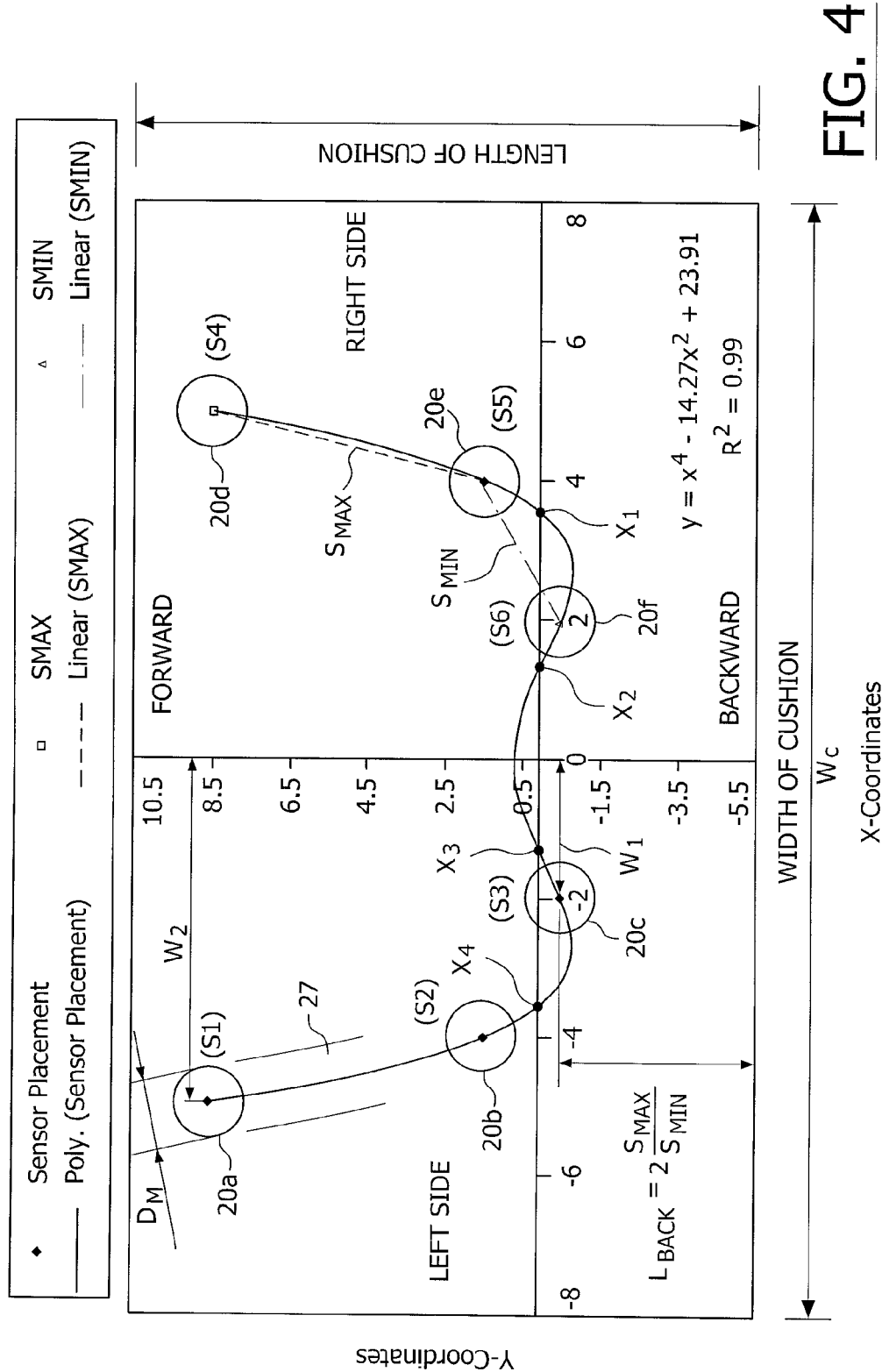
FIG. 4 illustrates in diagrammatic form an example location distribution of the force sensors within the cushion system of FIG. 3.

Reference is now made to FIG. 4, which illustrates in diagrammatic form an example position distribution of the force sensors 20 with respect to the cushion system 1 of FIG. 3. In some example embodiments, the design of the mechanical actuator system 22 provides a means of acquiring postural and pressure distributive data when placed underneath of a variety of existing wheelchair cushions 50. In order to accurately acquire the postural and pressure distributive data from a variety of patients with various anatomical structures, the force sensor 20 should be placed according to the layout and width of the sensing band 27. The width of the sensing band 27 is equivalent to the diameter of the effective area of the rigid round cap 21, which assists in concentrating the pressure from any point across the width of the band above the sensor to the center of the round active area 15a. In the example embodiment shown in FIG. 4, the sensing band 27 includes two symmetrical branches. The left hand branch is composed of sensors S1 (20a), S2 (20a) and S3 (20c), and the right hand branch is composed of sensors S4 (20d), S5 (20e) and S6 (20f). In some example embodiments, six or less sensors 20 are required to detect a suitable amount of force and provide a suitable response thereto. The sensing band 27 is offset from the back of the cushion system 1 wherein the perpendicular distance to the back row sensors S3 (20c) and S6 (20f) of each branch respectively is given by the distance of $L_{BACK}$. $L_{BACK}$ is proportional to the ratio between the maximum distance between the sensors and the minimum distance between the sensors 20 as shown in FIG. 4. The two sensors of each branch of the sensing band 27 between which the distance is $S_{MIN}$ are located towards the back of the cushion system 1. The single sensor 20 in each branch which is located further away, specified by the distance $S_{MAX}$ are located towards the front of the cushion system 1.

The profile of the sensing band 27 and the location of the sensors 20 in the cushion system 1 are shaped according to the quartic function in Equation 3, which may for example have a coefficient of determination of $R^2 \approx 0.99$.

Equation 3:

$$y = ax^4 + bx^3 + cx^2 dx + e \qquad (3)$$

The quartic function of Equation 3 contains geometrical parameters related to the design characteristics of the cushion system 1. Coefficients a, b, c, d and e are determined from the roots of the quartic function by the relationships shown in the system of Equation 4, which specify the shape of the sensing band 27.

Equation 4:

$$a = 1$$

$$-b = X_1 + X_2 + X_3 + X_4$$

$$c = X_1 \cdot X_2 + X_1 \cdot X_3 + X_1 \cdot X_4 + X_2 \cdot X_3 + X_2 \cdot X_4 + X_3 \cdot X_4$$

$$-d = X_1 \cdot X_2 \cdot X_3 + X_2 \cdot X_3 \cdot X_4 + X_1 \cdot X_2 \cdot X_4 + X_1 \cdot X_3 \cdot X_4$$

$$e = X_1 \cdot X_2 \cdot X_3 \cdot X_4 \qquad (4)$$

The symmetrical roots of the quartic are related to the sensor placement as shown in FIG. 4, where $X_1 = -X_4$ and $X_2 = -X_3$ For example, for the 16"×16" wheelchair cushion arrangement in FIG. 4, it was found that $X_1 = -X_4 = 3.59$ and $X_2 = -X_3 = 1.39$ which yield the following coefficients; a=1, b=0, c=14.27, d=0 and e=23.91 The relationship between the roots of the quartic function, the linear distance between the position of sensors, $S_{Max}$ and $S_{Min}$, the horizontal distance from S1 and S3 to the vertical axis, $W_2$ and $W_1$ as well as the width of the effective area of the cap, $D_M$, is given by Equation 5.

Equation 5

$$|D_M| = \frac{X_1}{X_2} = \frac{X_4}{X_3} = \frac{S_{MAX}}{S_{MIN}} = \frac{W_2}{W_1} \qquad (5)$$

In Equation 5, $S_{Max}$ is the maximum allowed linear distance between the sensors placed along the quartic function curve of sensor distribution band in the cushion system 1; and $S_{Min}$ is the minimum allowed linear distance between the sensors placed along the quartic function curve of sensor distribution band in the cushion system 1.

The sensors 20 are placed along the curvature described by Equations 3 and 5, as well as the $S_{Max}$ and $S_{Min}$ distances as illustrated in FIG. 4.

Figure 6:
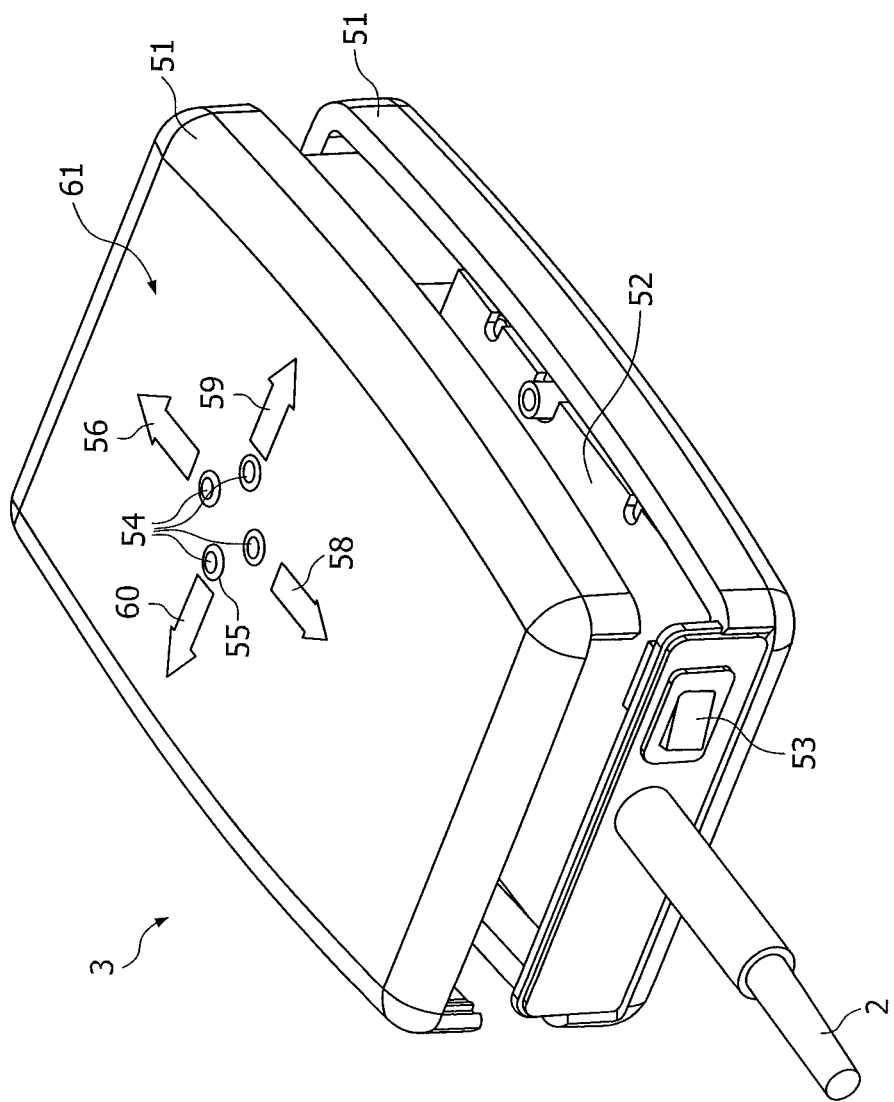
FIG. 6 shows an exploded perspective view of a control module to be used in the pressure monitoring system of FIG. 1.

Reference is now made to FIG. 6, which shows the control module 3 in detail. The FSRs 15 are connected to the input terminals of the control module 3 via a shielded multi-conducting cable 2. The control module is made of rigid plastic enclosure 51, which secures an electronic circuit board 52 inside. A top surface of the enclosure 51 includes an indicator system 61 which is powered by a battery (not shown) stored within a battery compartment (not shown). In other example embodiments, a solar battery is be used for powering of the indicator system 61 when exposed to the light. A multiple number of Light Emitting Diodes (LEDs) 54, for example four as shown, are mounted on top surface of the circuit board 52, so they stand upright towards the top surface of the control module enclosure 51. The top surface of the enclosure 51 has multiple numbers of holes 55 defined therein, for example four as shown, so the top of the LEDs 54 slightly penetrate through the top surface of the enclosure 51. The top surface of the enclosure 51 also includes a multiple number of arrow shape graphical indicators representing 56-forward, 58-backward, 59-right and 60-left, each corresponding to its own LED 54. An inner face of the control module 2 incorporates the main power-on switch 53. It can be appreciated that other suitable indicators and indicator systems may be used, and example embodiments may not be limited to the use of LEDs.

Figure 7:
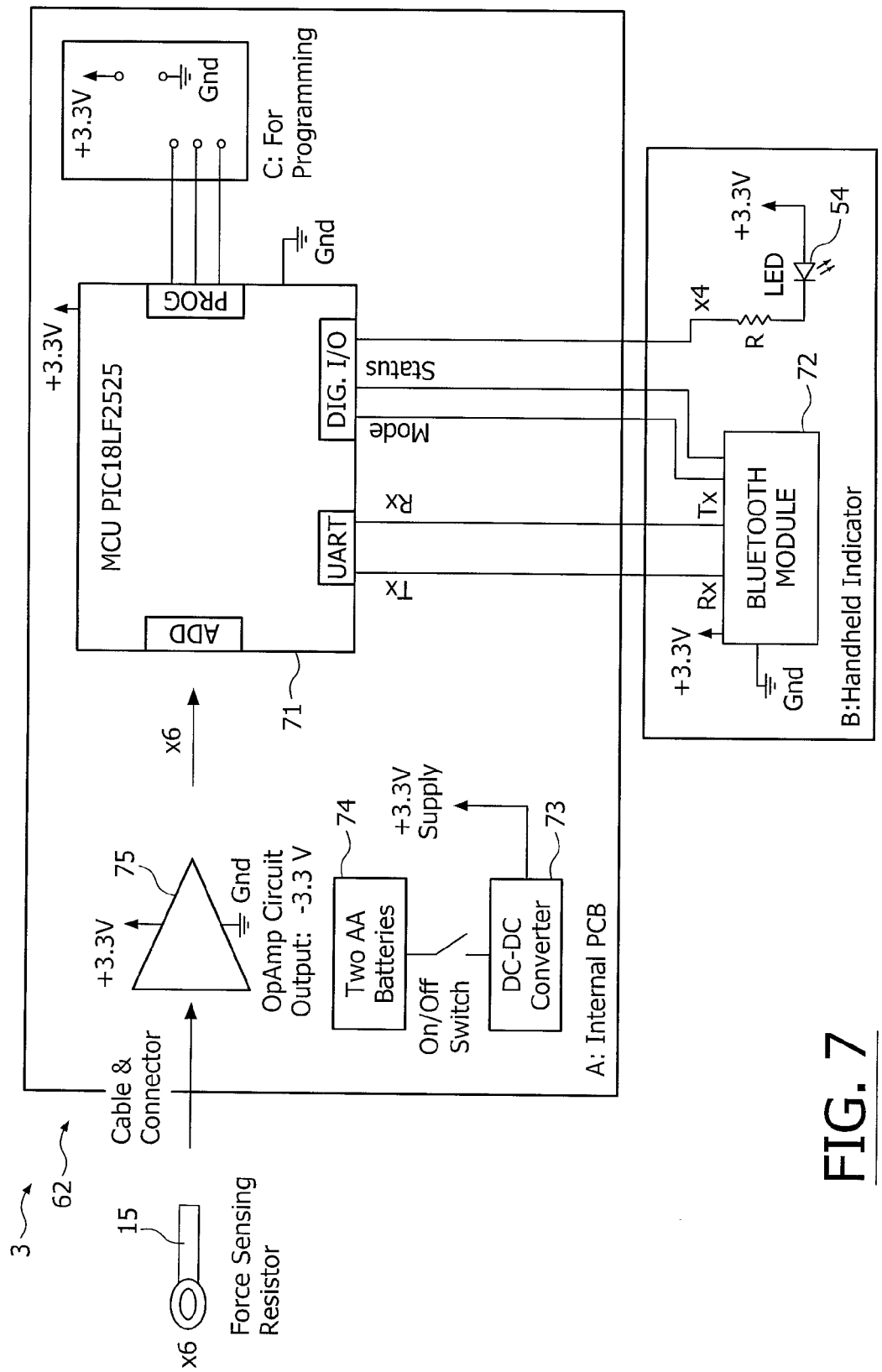
FIG. 7 illustrates in diagrammatic form an example electrical system block diagram of the control module of FIG. 6.

Reference is now made to FIG. 7, which illustrates in diagrammatic form an example electrical system block diagram 62 of the control module 3. The block diagram 62 acts as a controller of the pressure monitoring system 100. The block diagram 62 includes an 8-bit PIC microcontroller 71 with onboard Electrically Eraseable Programmable Read-Only Memory (EEPROM), a Bluetooth module 72, for example ESD200 and a DC to DC converter 73, which supplies power to the circuit from two AA rechargeable batteries 74. The sensing input is provided by the six Force Sensing Resistors (FSRs) 15, each connected to a non-inverting configuration operational amplifier 75, which provides an analog output proportional to the force applied to each sensor. One or more multiplexers (not shown) may be used with respect to the six FSRs 15. Each output of the non-inverting operational amplifier is connected to an Analog to Digital converter (ADC) channel. Four directional LEDs 54 are included in the system to provide feedback to the user regarding the user's posture alignment as well as their pressure distribution.

The Microchip PIC18LF2525 was selected as the 8-bit microcontroller 71 of the system. The microcontroller 71 has sufficient firmware memory to carry out the programmed operations and algorithms, including: reading the EEPROM on startup and setting up system parameters, reading the FSRs 15, performing posture and pressure distribution calculations, communicating with the Bluetooth module to provide wireless connectivity to the device, initiating the LED 54 alerts to specify areas of high pressure as well as the necessary corrective action required in the prevention of pressure ulcers.

The microcontroller 71 includes an onboard 8 MHz oscillator which provides the clock pulse required for all the timing and signal sampling. The microcontroller has an onboard 10 channel, 10 bit Analog to Digital converter (ADC) which digitizes the analog signal supplied from the sensor amplifiers. The microcontroller also has an Enhanced Universal Synchronous Asynchronous Receiver Transmitter (EUSART), which is used for communicating with the Bluetooth module 72. This allows for the device to be connected and updated wirelessly by a computer, a handheld wireless communication device, a smartphone or cellular phone. An interface for programming the firmware of the microcontroller 71 is also provided via header pins on the circuit board. The FSRs 15 provide a linear relationship between the force applied and the conductance through the force sensors 20. As the force applied on the force sensor 20 increases, the resistance of the force sensor 20 decreases thus increasing its conductance. The FSRs 15 are connected to non-inverting operational amplifiers in order to convert the force versus conductance relationship to an analog voltage within a specific range. As more force is applied to the FSRs 15 the higher the output voltage of the non-inverting operational amplifier. The non-inverting amplifiers are connected to the analog inputs and are sampled by the 10 bit ADC. The values are then processed by the microcontroller and undergo posture and pressure distribution tests as specified in the software algorithm. In an example embodiment, values are sampled at a specified time interval, for example every five seconds.

The Bluetooth module 72 is discoverable by other Bluetooth enabled devices and after supplying a handshaking pin code can receive information regarding the patient's use of the cushion system 1. The physician or therapist can also update certain values through the Bluetooth module 72 allowing for customization of the pressure distribution mode alerts for each patient. The DC circuit voltage is supplied by a DC to DC converter 73 which is powered by two AA rechargeable batteries 74 located inside the control unit. The low power amplifiers, microcontroller 71 and Bluetooth module 72 prolong the life span of the batteries.

Figure 8:
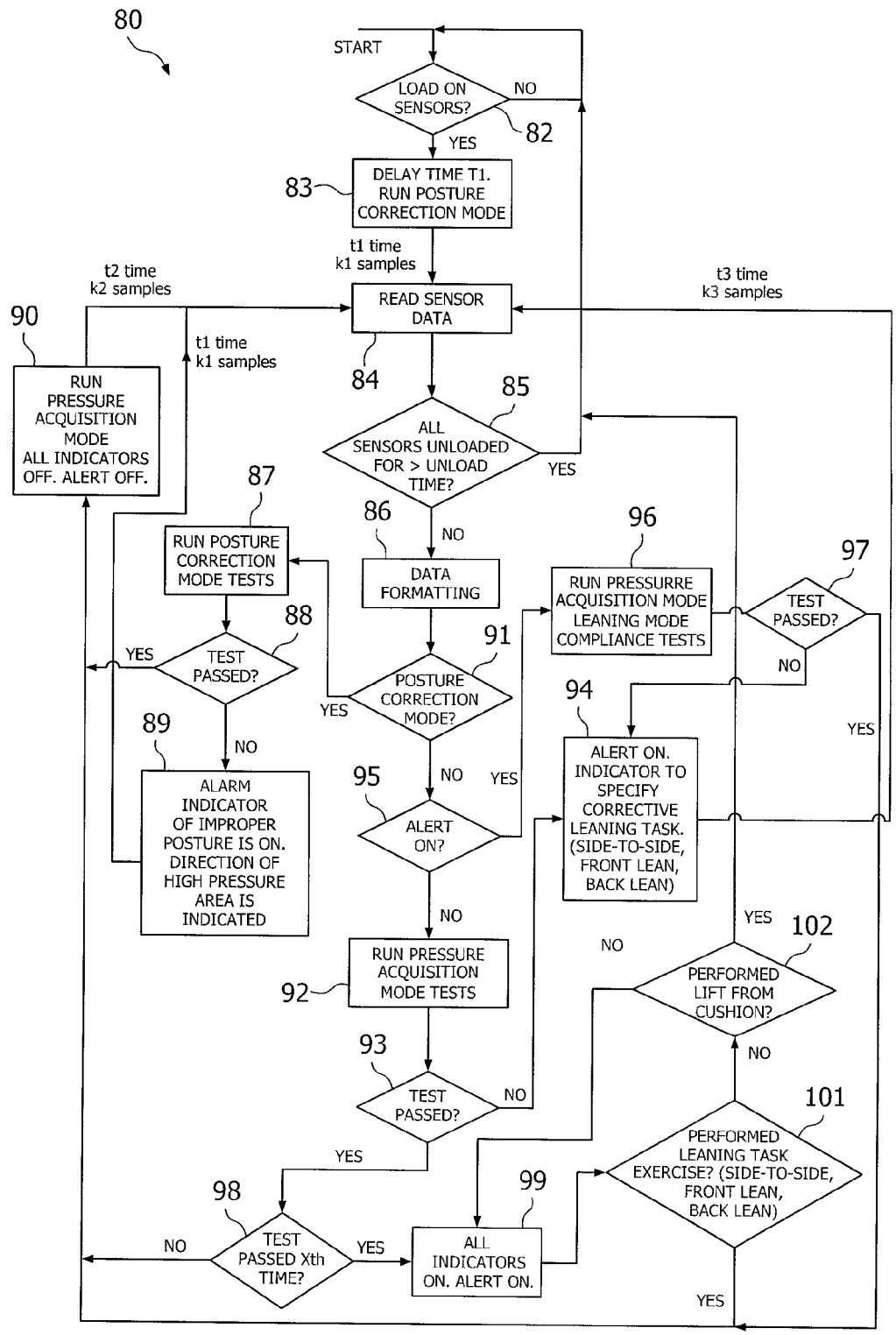
FIG. 8 illustrates in diagrammatic form a process to be implemented by the controller shown in FIG. 7 in accordance with an example embodiment.

Reference is now made to FIG. 8, which illustrates an example process 80 which illustrates an example logical operation of the microcontroller 71. The specific order of the processes in process 80 may vary according to the particular application, and in some embodiments more or less processes may be required. Further, various processes may be combined into one process or split into sub-processes. Upon the supply of power to the system by the actuation of the on switch 53 the system performs initializations, turns on all of its indicating LEDs 54 and at process 82 waits until it detects any load on the cushion system 1, as acquired by the ADC. Once the load is detected the system proceeds to process 83 waits a programmed delay time, $T_1$ and then enters the Posture Correction Mode of operation. During this mode the sensors are read (process 84) for a programmed period of time, $t_1$ and $k_1$ number of samples is collected. This process is indicated to the user via a counter-clockwise cycling of the LEDs 54. At process 85, it is determined whether that all the sensors have not been unloaded for longer than UnLoad time, and if so the acquired data is formatted (process 86), and is fed through the posture correction mode tests (process 87). At process 88, it is determined whether the posture correction tests are passed. If the patient's posture did not pass the outlined tests, at process 89 the patient is informed about their incorrect posture via the flashing indicating LEDs 54, which corresponds to the direction of the area of higher pressure and thus specifies the direction away from which the patient is required to move to correct their posture. Data collection of $k_1$ number of samples over $t_1$ time, formatting and tests are repeated again. If the tests are passed, at process 90 all indicating LEDs 54 are turned off and the system enters the Pressure Acquisition Mode (process 92), which is determined at decision block 91. In the Pressure Acquisition mode (process 92) the system acquires $k_2$, number of samples of sensor data over $t_2$ time. Once $t_2$ time has elapsed the system begins to format the data collected and automatically proceeds to execute the pressure acquisition mode tests as outlined in FIG. 9. At decision block 93, it is determined whether the Pressure Acquisition Mode tests were passed. If the system detects that the pressure distribution does not pass the pressure acquisition tests, an alert is activated at process 94 which is detected at decision block 95. The alert is used to alert the user to perform a Pressure Acquisition Mode Compliance test, at process 96. Examples of Acquisition Mode Compliance test include, for example having the user perform one of four corrective actions (Side-To-Side Lean Left, Side-To-Side Lean Right, Forward Lean, and Backward Lean) to remedy the possibly harmful pressure distribution situation. The necessary corrective action is specified by the flashing LEDs 54 corresponding to the required direction of motion. The system then acquires $k_3$ number of samples over $t_3$ time, formats the data and runs through the leaning task compliance tests (process 96). At decision block 97, it is determined whether the user is successful in complying with the tests, and if so at process 90 the LED 54 alerts are turned off and the system restarts the Pressure Acquisition mode (e.g., process 87). At process 98, if the Pressure Acquisition Mode tests are passed more than X times and no corrective actions were administered, the system begins to flash all the LEDs 54 in order to indicate that any one of the four corrective actions is required. At process 99, 101 and 102, if the user does not comply by performing the leaning task exercises, the system verifies that the patient did not unload all the sensors for more than UnLoad time and notifies that a corrective action is required again. Once the user complies with the required tasks the system returns to the Pressure Acquisition mode of operation (process 92) and begins to sample sensor data at $k_2$ number of samples over $t_2$ time. If the system detects that the user has unloaded all the sensors for more than UnLoad time the system automatically restarts and waits for the sensors to be loaded, which would then cause the system to automatically restart in the Posture Correction Mode again (process 96).

Reference is now made to FIG. 9B, which illustrates the data formatting process 86 in accordance with an example embodiment. The data formatting process 86 may reference values received from the force sensors 20a to 20e as positioned according to FIG. 9A. The data formatting process 86 generally processes received values and calculates additional values, which are used in other processes of the process 80. In example embodiments, one subset of sensors 20 may be used for comparing to another subsets of sensors. As shown, the Total Left Side is determined from the sum of sensors S1 (20a), S2 (20b) and S3 (20c). The Total Right Side is determined from the sum of sensors S4 (20d), S5 (20e) and S6 (20f). The Total Forward is determined from the sum of sensors S1 (20a) and S4 (20d). The Total Middle is determined from the sum of sensors S2 (20b) and S5 (20e). The Total Back is determined from the sum of sensors S3 (20c) and S6 (20f). The Total Back Four is determined from the sum of sensors S2 (20b), S3 (20c), S5 (20e), S6 (20f).

Reference is now made to FIG. 9C, which illustrates the posture correction mode tests (process 87) in accordance with an example embodiment. In the posture correction mode tests, specified values from one subset of sensors 20 are compared by subtracting the values from another subset of sensors 20 and determining whether a threshold between the values has been exceeded. If so, the indicator system 61 is controlled to advise the user of where the threshold has been exceeded. As illustrated in FIG. 9C, if the difference between Total Left Side and Total Right side exceed a Left Threshold, then the indicator system 61 indicates leaning too far left (i.e., left LED 54). The required user response is to lean towards the center so that the difference between Total Left Side and Total Right side becomes within the Left Threshold. In other words, the posture of the user is to be corrected by centering of the user. If the difference between Total Right Side and Total Left side exceed a Right Threshold, then the indicator system 61 indicates leaning too far right (i.e., right LED 54). If the Total Forward exceeds a Forward Threshold or the difference between Total Middle and Total Back exceeds a Back threshold, then the indicator system 61 indicates leaning too far forward (i.e., forward LED 54). If Total Back exceeds Total Middle and Total Back Four exceeds an All Back Threshold, then the indicator system 61 indicates leaning too far forward (i.e., backward LED 54).

Reference is now made to FIG. 9D, which illustrates the pressure acquisition mode tests (process 92) in accordance with an example embodiment. In the pressure acquisition mode tests, specified values from one subset of sensors 20 are compared by subtracting the values from another subset of sensors 20 and determining whether a threshold between the values has been exceeded. If so, the indicator system 61 is controlled to advise the user of the corrective responsive action to be taken by the user. Example responsive actions include specified exercises such as Do Side-to-Side Left Lean, Do Side-to-Side Right Lean, Do Lean Backward for a specified duration, and Do Lean Forward for a specified duration. Reference to lean includes having the user perform a pressure redistribution in the indicated direction or directions. In example embodiments, such exercises may include responsive actions which are more than merely righting the pressure distribution, but rather requiring the user to at least lean in an opposing direction for a duration of time. As illustrated in FIG. 9D, if the difference between Total Left Side and Total Right side exceed a Left Threshold 2, then the required user response is Side-to-Side Left Lean (as in process 96, FIG. 9E). If the difference between Total Right Side and Total Left side exceed a Right Threshold 2, then the required user response is Side-to-Side Right Lean (as in process 96, FIG. 9E). If the difference between Total Back and Total Forward is within the Back Threshold 2, then the required user response is Lean Backwards for a specified duration (as in process 96, FIG. 9E). If the difference between Total Back and Total Forward exceeds a Forward Threshold 2, then the required user response is Lean Forwards for a specified duration (as in process 96, FIG. 9E).

Reference is now made to FIG. 9E, which illustrates the pressure acquisition mode compliance tests (process 96) in accordance with an example embodiment. In the pressure acquisition mode compliance tests, the specified exercises are implemented step-by-step, with each step being indicated to the user and monitored for compliance. Again, these exercises may include responsive actions which are more than merely righting the pressure distribution, but rather may require the user to at least lean in an opposing direction for a duration of time and exceed a threshold of pressure in the opposing direction. Such an action or actions may provide corrective pressures at the contact areas for the user, for example by having the user lean to an opposing side.

Referring still to FIG. 9E, for the Side-to-Side Left Lean, the following processes occur in sequence: i) the left indicator is flashed until it is determined whether the difference between Total Left Side and Total Right Side exceeds a Left Threshold 3 for a duration Q time; ii) the right indicator is flashed until it is determined whether the difference between Total Right Side and Total Left Side exceeds a Right Threshold 3 for a duration Q time; and iii) the left indicator is flashed until it is determined whether the difference between Total Left Side and Total Right Side exceeds a Left Threshold 3 for a duration Q time.

Referring still to FIG. 9E, for the Side-to-Side Right Lean, the following processes occur in sequence: i) the right indicator is flashed until it is determined whether the difference between Total Right Side and Total Left Side exceeds the Right Threshold 3 for a duration Q time; ii) the left indicator is flashed until it is determined whether the difference between Total Left Side and Total Right Side exceeds the Left Threshold 3 for a duration Q time; and iii) the right indicator is flashed until it is determined whether the difference between Total Right Side and Total Left Side exceeds the Right Threshold 3 for a duration Q time.

Referring still to FIG. 9E, for Lean Backwards, the back indicator is flashed until the difference between Total Back and Total Middle exceed a Middle Threshold for a duration E time. For Lean Forwards, the forward indicator is flashed until the difference between Total Back and Total Middle is within a Back Threshold 3 for a duration R time.

It can be appreciated that reference to "sides" of the cushion system 1 are used for reference purposes with respect to the particular application and orientation of the user, and may not necessarily be limited to, for example, a reference to opposing sides of a centre line of the cushion system 1.

It can also be appreciated that some example embodiments may be readily integrated with existing wheelchairs and wheelchair cushions.

Some example embodiments may therefore be used for alerting individuals with spinal cord injury (SCI), who are sitting, whether they are sitting with a correct posture as well as indicate how to perform postural exercises to prevent skin breakdown. The example embodiments may provide a system for posture correction and pressure sore prevention. Such embodiments may for example be used by a physician, occupation therapist, as well as the patient.

In some example embodiments, the monitoring system 100 may be used to alert the user of a responsive action or responsive exercise to be taken, as well as assist in training the user (e.g., an SCI patient) to learn how to manage pressure during sitting. The monitoring system 100 may be integrated into the patient's wheelchair as part of their rehabilitation training. The system may also be used to longitudinally monitor how patients sit in their daily activities and that way help occupational therapists improve their sitting strategies, cushions and wheelchairs to provide customized sitting solutions for their patients. Current methods used to tune cushions and wheelchairs are static in nature, and do not adequately capture challenges pertaining to sitting posture experienced by the SCI individuals in their daily activities.

Some example embodiments of the monitoring system may, for example, be used by occupational therapists. Since occupational therapists have to move patients from in and out of their chairs the system could be used as a verification tool by the occupational therapist that the patient they have recently moved into the chair is sitting properly. The system will notify the patient or therapist about the status of their posture and pressure distribution in an unobtrusive and non-embarrassing manner; training of posture and pressure correction will periodically be reinforced.

Figure 10:
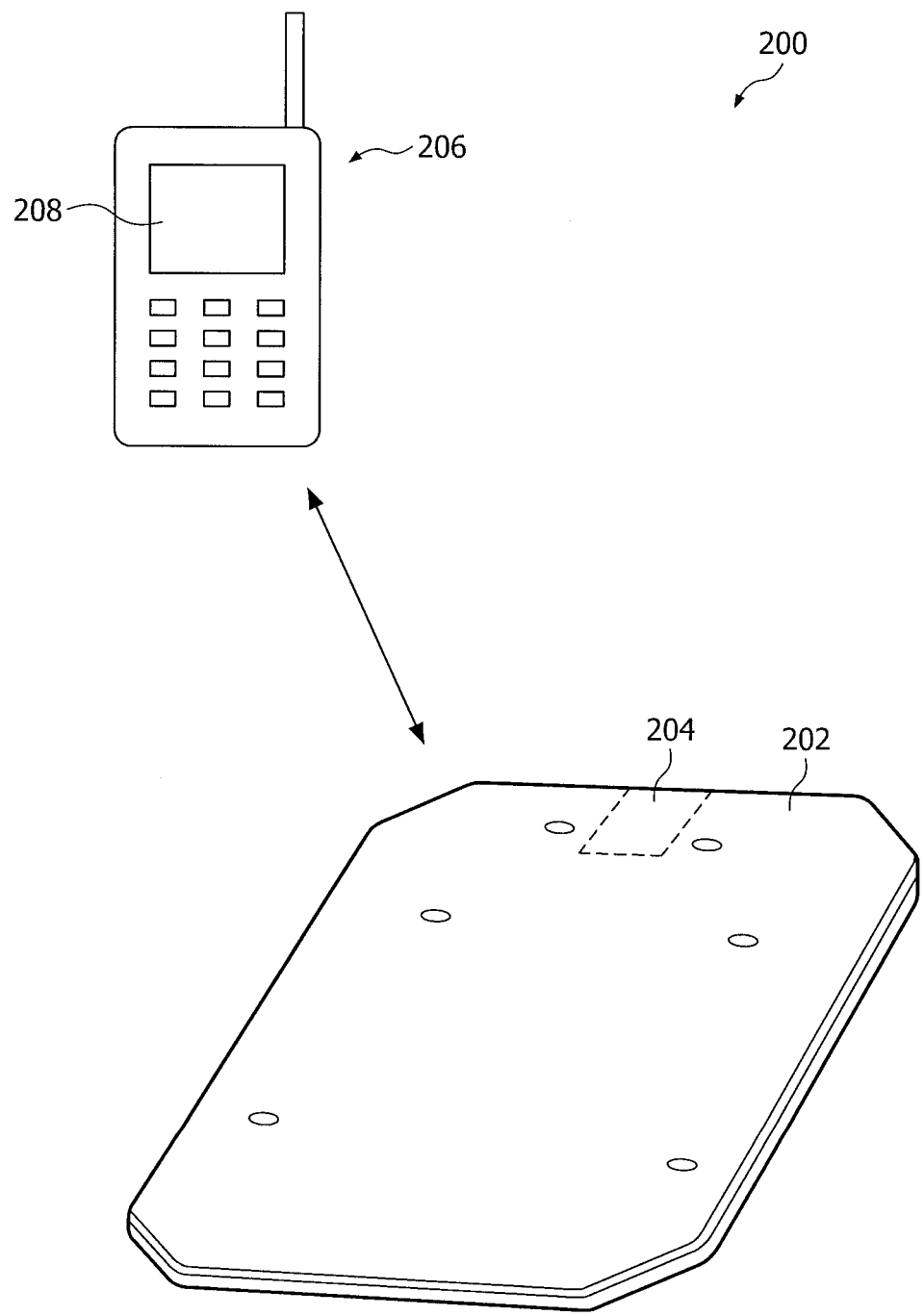
FIG. 10 shows a perspective view of a pressure monitoring system including a wireless communication device in accordance with another example embodiment.

Variations may be made in some example embodiments. Referring again to FIG. 1, some example embodiments do not include the multi-conducting cable 2. Thus, reference is now made to FIG. 10, which shows a pressure monitoring system 200 in accordance with another example embodiment. In the example shown, a cushion system 202 has included therein a controller 204. The controller 204 may include at least some or all of the components of the electrical system block diagram 62 (FIG. 7), including the Bluetooth module 72 (FIG. 7) or other communication submodule. The Bluetooth module 72 (FIG. 7) may be used for wireless communication with another wireless communication device 206, such as a computer, a handheld wireless communication device, a smartphone or cellular phone. The wireless communication device 206 may include a dedicated application for communication with the controller 204. The wireless communication device 206 further includes a display screen 208 which provides a user interface to display the various indicators to the user, and to receive user input when necessary.

Figure 13:
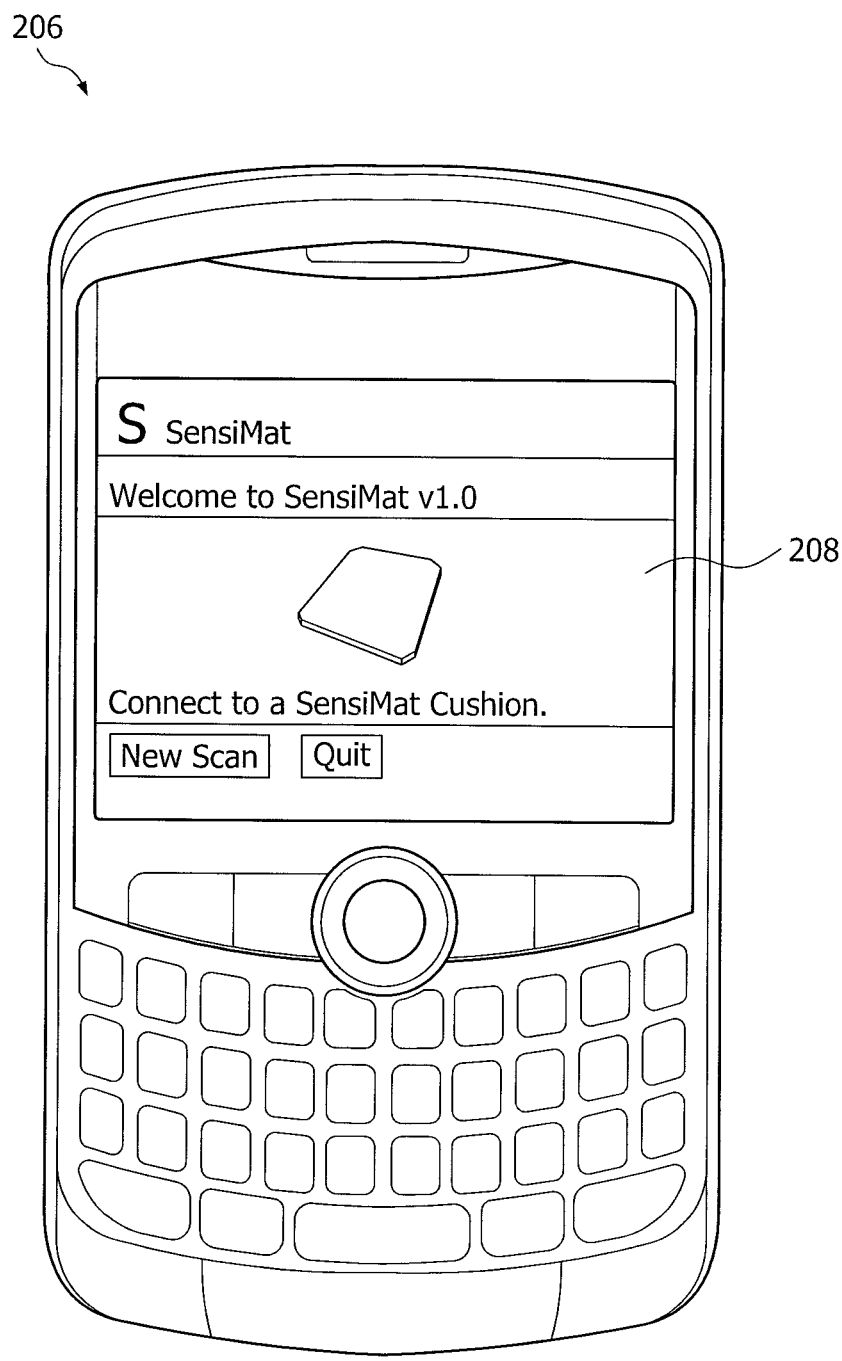
FIG. 13 illustrates an example user interface displayed on a display screen of the wireless communication device of FIG. 10, displaying a new scan screen.
Figure 14:
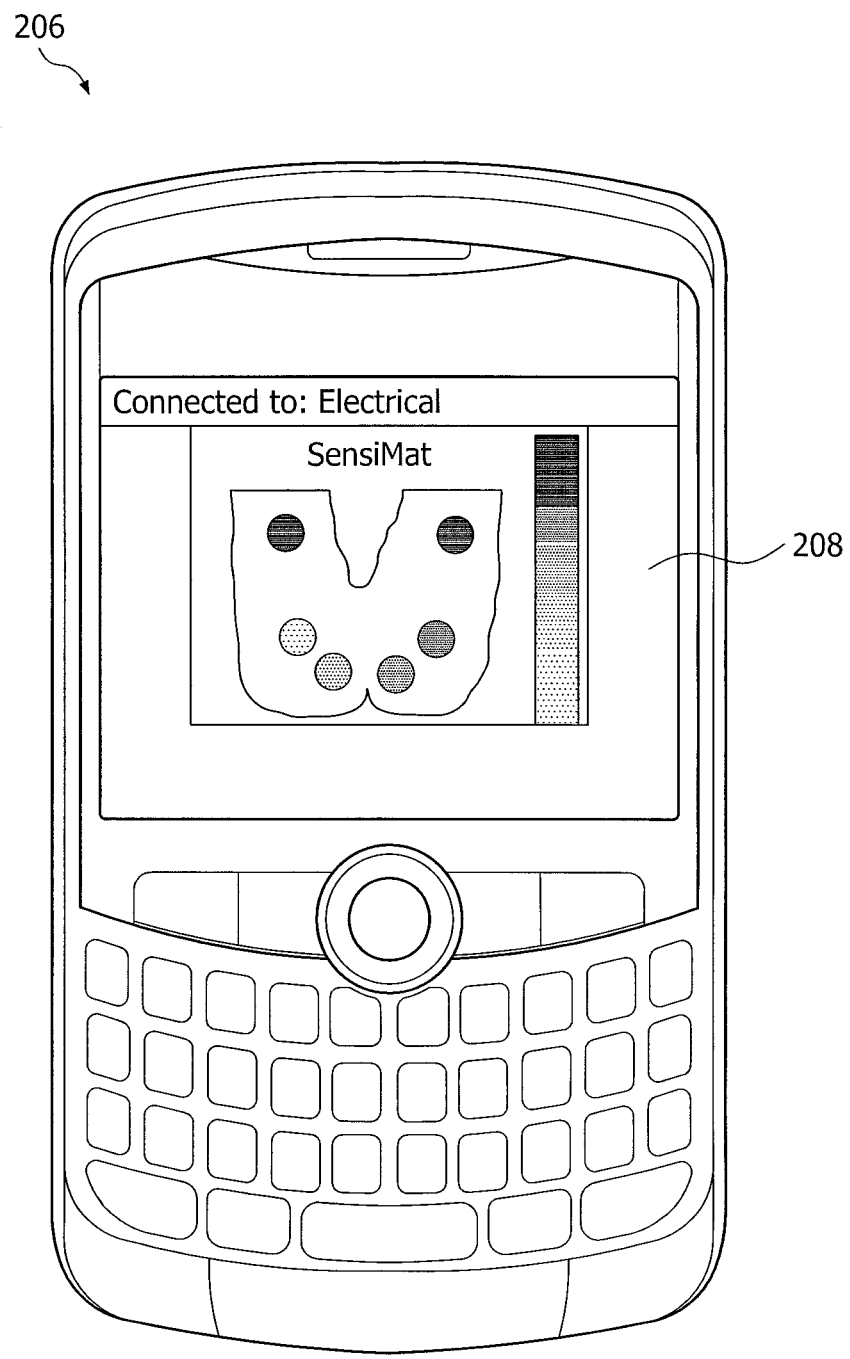
FIG. 14 illustrates an example user interface displayed on the display screen of the wireless communication device of FIG. 10, displaying pressure readings of a user having correct posture.
Figure 15:
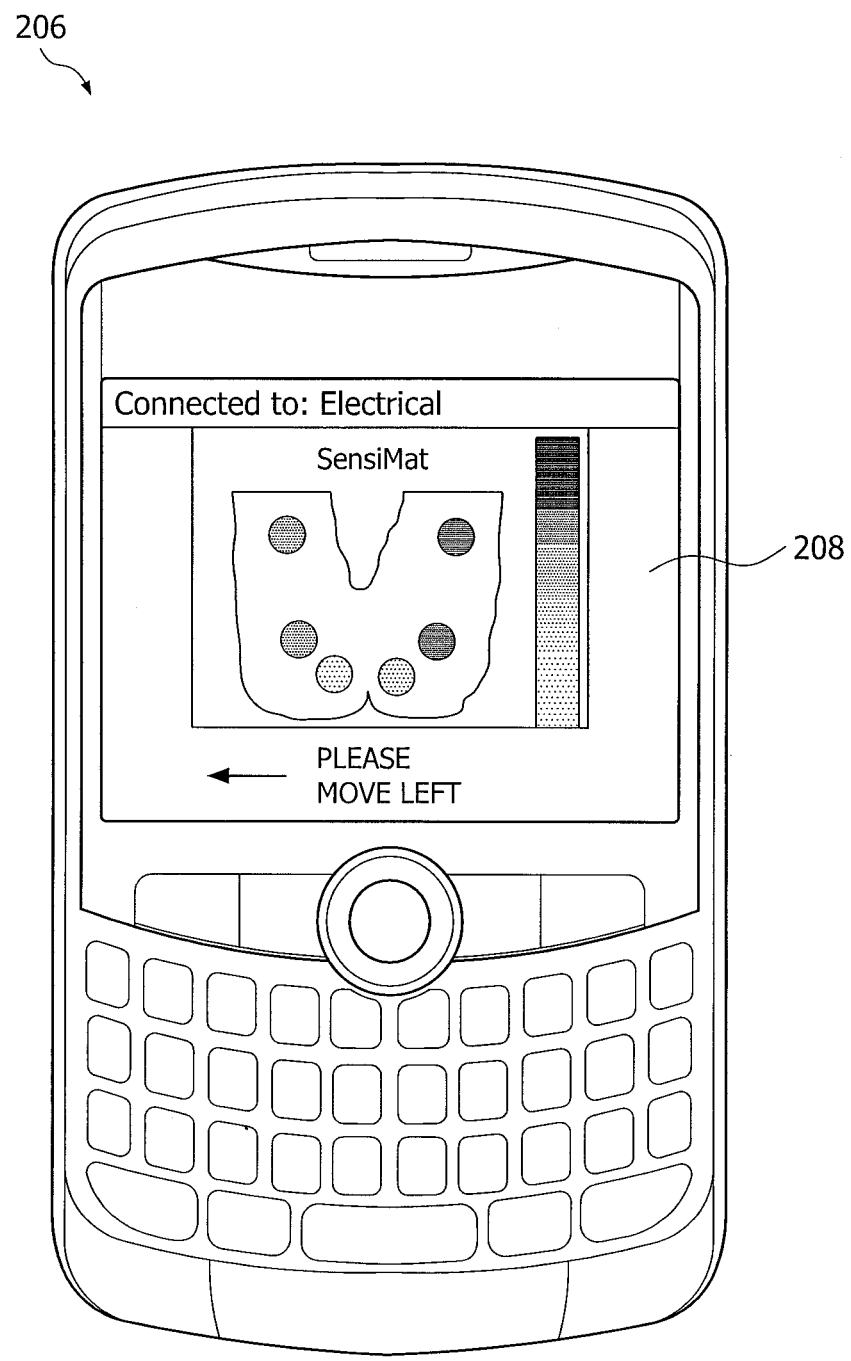
FIG. 15 illustrates an example user interface displayed on the display screen of the wireless communication device of FIG. 10, displaying a posture correction mode.

Reference is now made to FIGS. 13 to 15, which illustrate example user interfaces as displayed on the display screen 208. As shown, FIG. 13 illustrates an example user interface for a new scan screen. When the user is seated, the user may select the "New Scan" icon to initiate an application resident on the wireless communication device, which further initiates the cushion system 202. In other example embodiments, the resident application and/or the monitoring system 1 are automatically activated when the user sits on the cushion system 202. FIG. 14 displays pressure readings of a user, wherein the intensity of the pressure readings are represented by color and shade. As the pressure increases the shading and color will change from blue to green, then to yellow/orange followed by red. The shadings are used to indicate the increase in pressure in each color region, as darker shading indicates higher pressures and lighter shading indicates lower pressures (or vice versa in other embodiments). In the user interface shown, the user has correct posture and accordingly no additional instructions are displayed on the display screen 208. FIG. 15 illustrates the posture correction mode of the cushion system 202. In the example shown, there is a higher pressure detected at the right side of the cushion system 202, and accordingly the display 208 indicates that the user is to move left.

It can be appreciated by these example user interfaces that additional user interfaces, not shown, may be displayed on the display screen 208. These additional user interfaces may be used for the other indicators and instructions to be provided to the user, as described in detail with respect to FIGS. 8 and 9B to 9E.

Figure 11B:
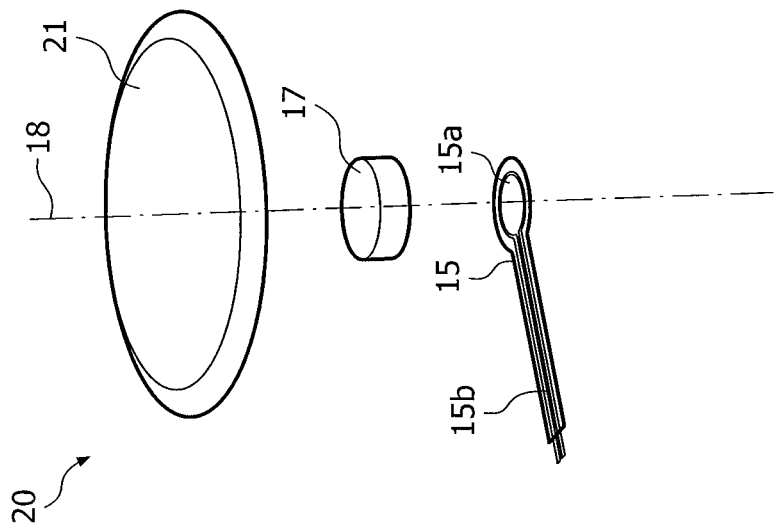
FIG. 11B shows an exploded perspective view of the force sensor shown in FIG. 11A.
Figure 11A:
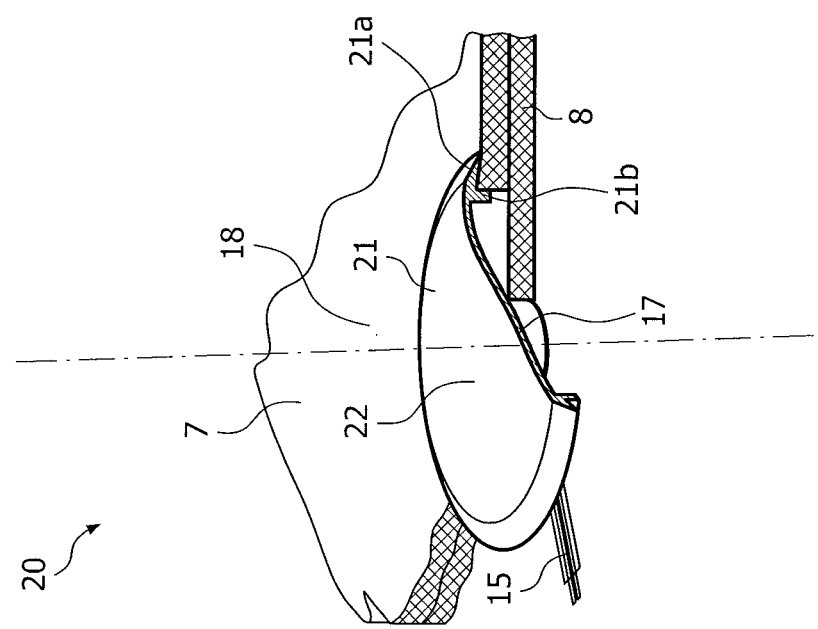
FIG. 11A shows a perspective partial view of a pressure monitoring system including a force sensor in accordance with another example embodiment to be used therein.
Figure 12:
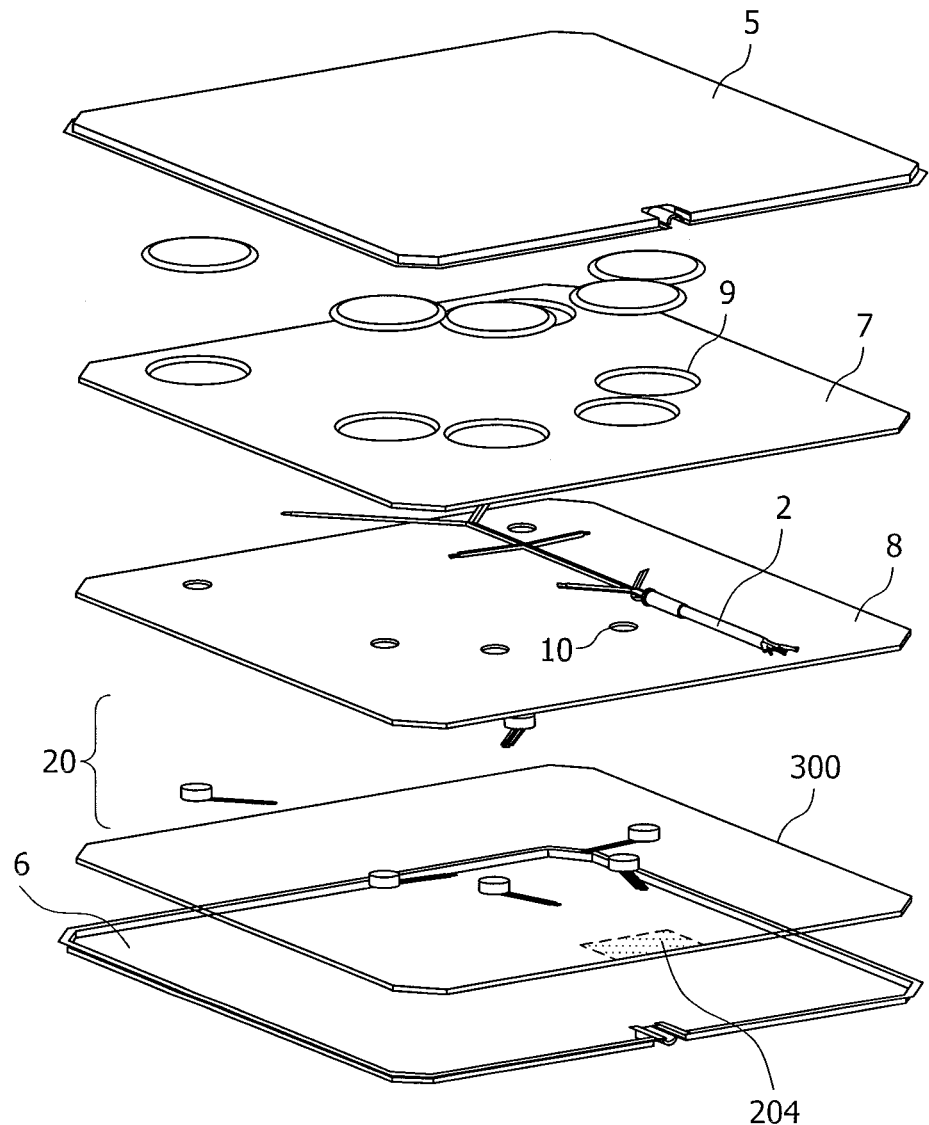
FIG. 12 shows an exploded perspective view of a cushion system including the force sensor actuator shown in FIGS. 11A and 11B in accordance with another example embodiment.

Reference is now made to FIGS. 11A, 11B and 12, which show the sensors 20 and cushion system 1 in accordance with another example embodiment. Similar reference numbers are for convenience and ease of reference. In this embodiment, individual rigid pads 12 (as in FIGS. 2A and 2B) are not used. Instead, a plate 300 which is shaped to generally correspond to the shape of the layers of the cushion system 1 is used for mounting of the force sensors 20. In the example shown in FIG. 12, the cushion system has included therein a controller 204. The controller 204 may include at least some or all of the components of the electrical system block diagram 62 (FIG. 7), including the Bluetooth module 72 (FIG. 7) or other communication submodule.

Although some embodiments of the system has been described with respect to wheelchairs and wheelchair cushions, it can be appreciated that example embodiments may be suitably modified for use in mattresses wherein the user is lying. Example embodiments may also be applied to footwear related articles such as insoles, wherein the user may be standing with or without assistance. Example embodiments may also be applied to other suitable applications where prolonged pressure may be applied to or from a user which may result in pressure sores if left unattended. Example embodiments may be used in applications where pressure may be applied unevenly along a contact surface, and wherein a user response may be required to compensate for the unevenly applied pressure.

While example embodiments have been described in detail in the foregoing, it will be understood by those skilled in the art that variations may be made.

What is claimed is:

1. A method of monitoring pressure at a seat having a contact surface, the contact surface for engaging a user, the contact surface including a specified width ($W_C$), a median of the specified width, and a rear edge in relation to the contact surface of the seat, the method for prevention of pressure sores, the method being performed by a controller and comprising:

receiving a signal from each of a plurality of force sensors, the force sensors defining a sensing band and mounted in relation to the rear edge of the contact surface, the force sensors each providing said signal in proportion to an amount of force detected, each force sensor having an effective sensor width ($D_M$), wherein said $D_M$ is correlated to said $W_C$, said $D_M$ is correlated to a diameter (d) of a sensor actuator of the force sensors, and said $D_M$ is correlated to durometers of comprising materials of the sensor actuator ($DU_1$) and encompassing one or more layers of foam ($DU_2$), wherein said $D_M$ satisfies the following:

$$\frac{D_M}{d} = \frac{DU_1}{DU_2} = K, \ \frac{W_C}{D_M} = 2K, \ K = 3 - 3.5,$$

wherein the force sensors within the sensing band are positioned in relation to the contact surface in accordance with a quartic function, wherein the quartic function is symmetrical about the median of the contact surface, wherein the quartic function is of the form $y = ax^4 + bx^3 + cx^2 dx + e$, with coefficients $a = 1$ $-b = X_1 + X_2 + X_3 + X_4$ $c = X_1 \cdot X_2 + X_1 \cdot X_3 + X_1 \cdot X_4 + X_2 \cdot X_3 + X_2 \cdot X_4 + X_3 \cdot X_4$ $-d = X_1 \cdot X_2 \cdot X_3 + X_2 \cdot X_3 \cdot X_4 + X_1 \cdot X_2 \cdot X_4 + X_1 \cdot X_3 \cdot X_4$ $e = X_1 \cdot X_2 \cdot X_3 \cdot X_4$ and has symmetrical non-zero roots ($X_1, X_2, X_3, X_4$) which satisfy:

$$|D_M| = \frac{X_1}{X_2} = \frac{X_4}{X_3} = \frac{S_{MAX}}{S_{MIN}},$$

wherein $S_{MAX}$ is a maximum distance between the force sensors on each half of the sensing band and $S_{MIN}$ is a minimum distance between the force sensors on each half of the sensing band, wherein the sensing band is offset from the rear edge of the contact surface of the seat by a distance $L_{BACK}$ as follows:

$$L_{BACK} = 2 \frac{S_{MAX}}{S_{MIN}};$$

grouping force sensors into subset groups of the plurality of sensors based on location within the sensing band, including one side of the median, other side of the median, forward, middle, and back, determining one or more values associated with each force sensor;

calculating a difference between a first one or more values associated with a first subset group of force sensors with a second one or more values associated with a second subset group of force sensors;

determining from said difference whether a threshold between said first one or more values and said second one or more values has been exceeded over a period of time;

controlling, based on said determining, an indicator to provide an indication to the user to indicate a first responsive action, the first responsive action for performing a lean task towards said second subset group of force sensors, the first responsive action for increasing of pressure to said second subset group of force sensors; determining from the first and second one or more values associated with each force sensor whether said lean task has been satisfied by determining whether a second threshold has been exceeded by a calculated difference between said second one or more values and said first one or more values over a subsequent period of time, and in response to determining that said lean task has been satisfied outputting an indication of the second threshold being exceeded to the indicator.

2. A method as claimed in claim 1, wherein the first subset group of force sensors in the sensing band is located in relation to the one side of the median of the contact surface, and the second subset group of force sensors in the sensing band is located in relation to the other side of the median of the contact surface.

3. A method as claimed in claim 1, further comprising controlling, when said second threshold has been exceeded for a predetermined duration, the indicator to indicate a second responsive action, the second responsive action for performing a subsequent lean task towards said first subset group of force sensors, the second responsive action for increasing of pressure to said first subset group of force sensors.

4. A method as claimed in claim 3, further comprising determining whether said second responsive action has been satisfied by determining whether a third threshold has been exceeded between said first one or more values and said second one or more values.

5. A pressure monitoring system for prevention of pressure sores, the pressure monitoring system comprising:
a seat including a contact surface, the contact surface for engaging a user, the contact surface including a specified width ($W_C$), a median of the specified width, and a rear edge in relation to the contact surface of the seat;
a plurality of force sensors defining a sensing band and mounted in relation to the rear edge of the contact surface, the force sensors each providing a signal in proportion to the amount of force detected, each force sensor having an effective sensor width ($D_M$),
wherein said $D_M$ is correlated to said $W_C$, said $D_M$ is correlated to a diameter (d) of a sensor actuator of the force sensors, and said $D_M$ is correlated to durometers of comprising materials of the sensor actuator ($DU_1$) and encompassing one or more layers of foam ($DU_2$) for the force sensors, wherein said $D_M$ satisfies the following:

$$\frac{D_M}{d} = \frac{DU_1}{DU_2} = K, \frac{W_C}{D_M} = 2K, K = 3 - 3.5,$$

wherein the force sensors are positioned in relation to the contact surface in accordance with a quartic function, wherein the quartic function is symmetrical about the median of the contact surface, wherein the quartic function is of the form $y=ax^4+bx^3+cx^2dx+e$, with coefficients $a=1$ $-b=X_1+X_2+X_3+X_4$ $c=X_1 \cdot X_2+X_1 \cdot X_3+X_1 \cdot X_4+X_2 \cdot X_3+X_2 \cdot X_4+X_3 \cdot X_4$ $-d=X_1 \cdot X_2 \cdot X_3+X_2 \cdot X_3 \cdot X_4+X_1 \cdot X_2 \cdot X_4+X_1 \cdot X_3 \cdot X_4$ $e=X_1 \cdot X_2 \cdot X_3 \cdot X_4$ and has symmetrical non-zero roots ($X_1$, $X_2$, $X_3$, $X_4$) which satisfy:

$$|D_M| = \frac{X_1}{X_2} = \frac{X_4}{X_3} = \frac{S_{MAX}}{S_{MIN}},$$

wherein $S_{MAX}$ is a maximum distance between the force sensors on each half of the sensing band and $S_{MIN}$ is a minimum distance between the force sensors on each half of the sensing band,
wherein the sensing band is offset from the rear edge of the contact surface of the seat by a distance $L_{BACK}$ as follows:

$$L_{BACK} = 2\frac{S_{MAX}}{S_{MIN}};$$

a controller for receiving each signal from the plurality of force sensors and determining one or more values associated with each force sensor; and
an indicator in communication with the controller,
the controller being configured for:
grouping force sensors into subset groups of the plurality of sensors based on location within the sensing band, including one side of the median, other side of the median, forward, middle, and back,
calculating a difference between a first one or more values associated with a first subset group of force sensors with a second one or more values associated with a second subset group of force sensors,
determining from said difference whether a threshold between said first one or more values and said second one or more values has been exceeded over a period of time,
controlling, based on said determining, the indicator to provide an indication to the user to indicate a first responsive action, the first responsive action for performing a lean task towards said second subset group of force sensors, the first responsive action for increasing of pressure to said second subset group of force sensors;
determining from the first and second one or more values associated with each force sensor whether said lean task has been satisfied by determining whether a second threshold has been exceeded by a calculated difference between said second one or more values and said first one or more values over a subsequent period of time, and in response to determining that said lean task has been satisfied outputting an indication of the second threshold being exceeded to the indicator.

6. A pressure monitoring system as claimed in claim 5, wherein the first subset group of force sensors in the sensing band is located in relation to the one side of the median of the contact surface, and the second subset group of force sensors in the sensing band is located in relation to the other side of the median of the contact surface.

7. A pressure monitoring system as claimed in claim 5, wherein the controller is further configured for controlling, when said second threshold has been exceeded for a predetermined duration, the indicator to indicate a second responsive action, the second responsive action for performing a subsequent lean task towards said first subset group of force sensors, the second responsive action for increasing of pressure to said first subset group of force sensors.

8. A pressure monitoring system as claimed in claim 7, wherein the controller is further configured for determining whether said second responsive action has been satisfied by determining whether a third threshold has been exceeded between said first one or more values and said second one or more values.

9. A method as claimed in claim 1, further comprising the controller processing the one or more values associated with each force sensor to operate between a posture correction mode, a lean task mode, a pressure acquisition mode and an acquisition mode compliance.

10. A pressure monitoring system as claimed in claim 5, wherein the controller is further configured to process the one or more values associated with each force sensor to operate between a posture correction mode, a lean task mode, a pressure acquisition mode and an acquisition mode compliance.

11. A method as claimed in claim 1, wherein the controller includes a microcontroller.

12. A pressure monitoring system as claimed in claim 5, wherein the controller comprises a microcontroller.

13. A method as claimed in claim 1, wherein each of the force sensors comprises at least one force sensing resistor.

14. A pressure monitoring system as claimed in claim 5, wherein each of the force sensors comprises at least one force sensing resistor.

* * * * *